(12) United States Patent
Harley

(10) Patent No.: US 6,369,890 B1
(45) Date of Patent: Apr. 9, 2002

(54) PARTICLE SEPARATION AND DETECTION APPARATUS

(75) Inventor: Philip Harley, Hexham (GB)

(73) Assignee: Kidde Fire Protection Limited, Derby (GB)

( * ) Notice: Subject to any disclaimer, the term of this patent is extended or adjusted under 35 U.S.C. 154(b) by 0 days.

(21) Appl. No.: 09/101,421

(22) PCT Filed: Jan. 7, 1997

(86) PCT No.: PCT/GB97/00037

§ 371 Date: Dec. 4, 1998

§ 102(e) Date: Dec. 4, 1998

(87) PCT Pub. No.: WO97/25611

PCT Pub. Date: Jul. 17, 1997

(30) Foreign Application Priority Data

Jan. 10, 1996 (GB) .............................................. 9600444

(51) Int. Cl.$^7$ ............................................... G01N 21/00
(52) U.S. Cl. ...................... 356/337; 356/336; 356/343; 356/441; 250/574
(58) Field of Search ................................. 356/337, 338, 356/339, 340, 341, 342, 343, 438, 441; 250/574, 575, 524

(56) References Cited

U.S. PATENT DOCUMENTS

| 3,799,670 A | * | 3/1974 | Kohr .......................... 250/574 |
| 4,475,382 A | * | 10/1984 | Frank .......................... 356/343 |
| 4,769,550 A | * | 9/1988 | Dolnick ....................... 250/574 |
| 4,930,095 A | * | 5/1990 | Yuchi et al. ............. 364/571.01 |
| 5,218,771 A | * | 6/1993 | Redford ....................... 250/574 |
| 5,381,130 A | * | 1/1995 | Thuillard et al. ........... 356/438 |
| 5,411,682 A | * | 5/1995 | Nagashima ................. 356/338 |
| 5,719,557 A | * | 2/1998 | Rattman et al. ............ 356/339 |

FOREIGN PATENT DOCUMENTS

| EP | 0664445 | * | 12/1994 |
| GB | 2259761 | * | 3/1993 |

* cited by examiner

Primary Examiner—Frank G. Font
Assistant Examiner—Sang H. Nguyen
(74) Attorney, Agent, or Firm—Leydig, Voit & Mayer, Ltd.

(57) ABSTRACT

Particle detecting apparatus for detecting other particulate matter comprises a measuring section and an input/output section removably attached together. A measuring chamber receives gaseous fluid by diffusion from a receiving chamber connected via an inlet to an area being monitored. The measuring chamber comprises a cylindrical body housing pairs of light emitting diodes positioned diametrically opposite, and directing light towards, each other through a sampling volume viewed by a photo-diode through a viewing aperture. The photo-diode detects light scattered by particles in the sampling volume. A glass tube protects the LEDs from contamination and can easily be cleaned or removed. Each LED can temporarily be de-energised in turn so as to act as a light detector, its output in response to light received from the opposite LED being thus a measure of any contamination. The measuring and input/output sections can easily be separated for servicing or replacement.

29 Claims, 3 Drawing Sheets

PARTICLE SEPARATION AND DETECTION APPARATUS

BACKGROUND OF THE INVENTION

The invention relates to particle separation and detection apparatus. Apparatus embodying the invention, and to be described below by way of example only, is for detecting oil mist, such as may arise under fault conditions in internal combustion engines and which may present a fire or explosion hazard. However, apparatus embodying the invention may be used for many other applications.

According to the invention, there is provided particle detecting apparatus for detecting the presence of particles in gaseous fluid, comprising light sensing means positioned to have a field of view extending axially along a sensing chamber defined by wall means extending from the light sensing means to an open end for receipt of the gaseous fluid, and at least two light emitters mounted to direct emitted light across the chamber in opposite directions along a common light path towards a sensing volume positioned on the axis of the chamber, whereby particles carried by the gaseous fluid into the sampling volume scatter some of the light therein for detection by the light sensing means.

According to the invention, there is further provided apparatus for detecting particles within gaseous fluid, comprising a measuring chamber for receiving the gaseous fluid, light emitting means mounted to direct light into the measuring chamber, and light detecting means having a field of view extending in the chamber and mounted to produce an output in response to the effect of particles in the gaseous fluid in the chamber on the light produced by the light emitting means, the light emitting means comprising at least two light emitter units positioned to direct light in opposite directions along a common light path across the chamber, each unit being switchable into a light detecting mode in which it responds to light received from the other along the said light path unit and produces a corresponding output, the output being dependent on contamination in the said light path.

According to the invention, there is also provided particle detecting apparatus for detecting the presence of particles within gaseous fluid, comprising: measuring means and gaseous fluid input/output means; the measuring means comprising a measuring chamber for receiving a sample of the gaseous fluid, light emitting means emitting light into the measuring chamber, and light detecting means operative to produce an output dependent on the effect of any particles in the gaseous fluid in the measuring chamber on the light emitted by the light emitting means; the gaseous fluid input/output means comprising a gaseous fluid inlet for receiving gaseous fluid from an area to be monitored and directing it into a receiving chamber, and an outlet through which gaseous fluid from the receiving chamber is exhausted; the measuring means being mounted within a first housing and the gaseous fluid input/output means being mounted in a second housing, the two housings being removably attached together such that gaseous fluid in the receiving chamber can enter the measuring chamber by diffusion.

According to the invention, there is yet further provided cyclone apparatus for removing at least some particulate matter from gaseous fluid carrying it, comprising inner and outer cylindrical walls arranged coaxially to define an annular passage, an inlet for the gaseous fluid into the annular chamber and an outlet therefrom, the inlet and outlet being spaced axially along the annular chamber, the inlet extending in a radial direction with respect to the annular chamber whereby gaseous fluid entering the chamber is directed in a generally circular direction around the annular chamber from the inlet to the outlet and the said particulate matter tends to be deposited at least on the outer wall of the annular chamber by centrifugal force.

Oil mist detection apparatus embodying the invention will now be described, by way of example only, with reference to the accompanying diagrammatic drawings in which.

Figure 1:
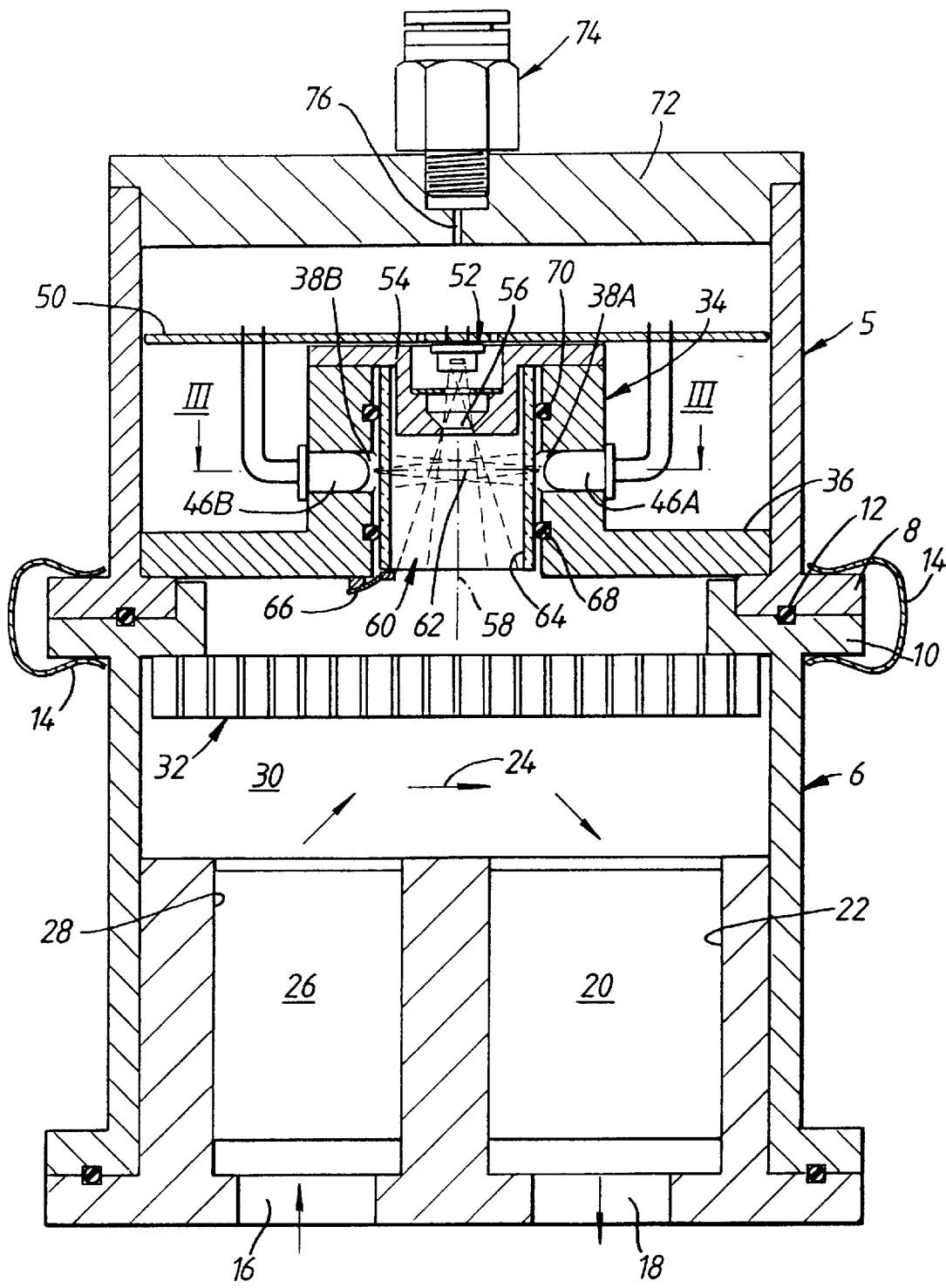
FIG. 1 is a cross-section through one form of the apparatus for explaining its operation.

Referring to FIG. 1, the apparatus comprises a measuring section 5 and an input/output section 6, each of generally cylindrical construction. The section 5 has a flange 8 which matches and is in contact with a flange 10 on the section 6, an "O"-ring 12 being interposed for sealing purposes. The flanges 8,10 are secured together such as by means of a simple clip shown diagrammatically at 14 or by means of bolts or other suitable means.

The section 6 defines an inlet 16 which in use is connected directly or by a suitable pipe to part of the engine which is being monitored, such as its crankcase. An outlet 18 is connected directly or by a suitable pipe to exhaust; normally, it will be connected back to the crankcase of the engine. A suitable fan 20 is mounted in a chamber 22. When energised, it draws air in through the inlet 16 from the engine and returns it through the outlet 18 as shown by the arrows 24. A suitable cyclone 26 is mounted in a chamber 28. The purpose of the cyclone is to impart circular motion to the incoming air so that gross particles of oil or other contamination are thrown outwardly by centrifugal force and deposited within the chamber 28. Any oil mist, which is to be detected by the apparatus, will not be removed by the cyclone 26.

A suitable form of cyclone embodying the invention will be described in more detail below with reference to FIG. 2.

The air drawn in by the fan 20 in the manner described passes through a receiving chamber 30 which is connected to the interior of the section 5 of the apparatus by means of a diffusion screen 32. The diffusion screen 32 may be omitted completely, however.

The diffusion screen 32 illustrated in FIG. 1 is made up of a plurality of tubes mounted side by side with their axes parallel to each other. Diffusion of the sampled atmosphere into the interior of the upper part 5 takes place largely as a result of Brownian motion of the particles. The smaller particles, which are the particles mainly intended to be detected by the apparatus, tend to move in straight lines and thus pass readily through the tubes of the diffusion screen 32. Larger particles, whose motion is less rectilinear, are more likely to be intercepted by and deposited on the interior walls of the tube.

Figure 3:
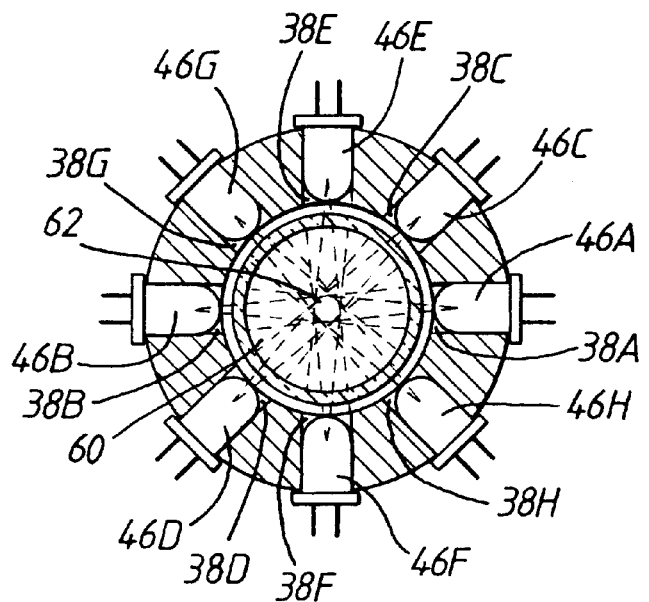
FIG. 3 is a diagrammatic cross-section on line III—III of FIG. 1.

The section 5 of the apparatus comprises a cylindrical body 34 which is supported on the flange 8 by means of its own flange 36. The cylindrical body 34 is provided with eight apertures extending in respective radial directions, of which two such apertures 38A and 38B are shown in FIG. 1, these apertures being arranged diametrically opposite each other across the cylindrical body 34. FIG. 3 shows how the other apertures are arranged in similar diametrically opposite pairs 38C and 38D, 38E and 38F, and 38G and 38H. A respective light emitting diode (LED) 46A . . . 46H is mounted within each aperture 38A, . . . 38H.

A printed circuit board 50 extends across the interior of the section 5 and supports the electrical circuitry of the apparatus. Centrally of this circuit board 50 is mounted a photo-diode 52 which is supported in an end cap 54 of the cylindrical body 34. The end cap 54 is shaped to define a narrow viewing aperture 56 which is centred on the axis 58 of the cylindrical body 54.

Each of the LEDs 46A . . . 46H is designed to produce a narrow beam of light which is directed diametrically across a measuring chamber 60 as shown by the dotted lines. The light outputs of all the LEDs thus intersect in a sampling volume 62. This sampling volume is viewed by the photo-diode 52 through the aperture 56.

An open-ended glass tube 64 is mounted within the measuring chamber 60 within the cylindrical body 34. It is held in position by a suitable clip such as shown diagrammatically at 66 and rests in contact sealing rings 68 and 70.

The light emitted by the LEDs 46A . . . 46H passes through the glass tube 64 with only minimal effect on the light.

The top of the section 5 is closed off by a lid 72 which supports an inlet 74 for clean air. This air passes through a bore 76.

The operation of the apparatus will now be described.

When the fan 20 is energised, air is drawn from the interior of the engine together with oil mist and any other contamination. In the manner already explained, the cyclone 26 will remove gross particles. Further relatively large particles may be removed by the diffusion screen 32 (if present).

Any oil mist or other particles diffusing into the interior of the measuring chamber 60 will enter the sampling volume 62 and will scatter some of the light from the LEDs 46A . . . 46H towards the photo-diode 52 which will produce a consequent warning output, indicating the presence of the particulate contamination.

The geometrical arrangement within the measuring chamber 60 is such that, in the absence of any particles, the photo-diode 52 has a completely dark view. The viewing aperture 56, and the arrangement of the LEDs so that their light is directed substantially at 90 degrees to the viewing direction of the photo-diode 52, ensure that the photo-diode cannot receive light directly from the LEDs but only when that light is scattered by particulate contamination.

The aperture 56 is arranged so that the photo-diode 52 cannot view any portion of the wall of the glass tube 64 which might otherwise conduct some of the light from the LEDs into a position in which it was visible to the photo-diode.

The glass tube 64 protects the LEDs themselves from receiving deposits of contamination from the sampled atmosphere. Any such deposits, being close to the actual source of the light, could refract the light towards the viewing aperture 56. Furthermore, it would be very difficult to clean any such contamination from the LEDs because of the shape of their emitting surfaces and because they are partially recessed within the radial cavities 38A . . . 38H. Any such contamination on the interior surface of the glass tube 64 will have less refracting effect on the light emitted by the LEDs. More importantly, however, it can much more easily be cleaned off the surface of the glass tube 64, or the glass tube may be removed and replaced. This cleaning or replacement process is eased by the fact that the sections 5 and 6 can rapidly be separated.

Although removal of such contamination is relatively simple, it is necessary to ensure that contamination does not build up to such an extent during operation of the apparatus that it adversely affects its detection ability. In accordance with a feature of the invention, therefore, the apparatus is arranged automatically to carry out a check for the presence of any contamination obscuring the light outputs of the LEDs 46A . . . 46H.

Figure 4:
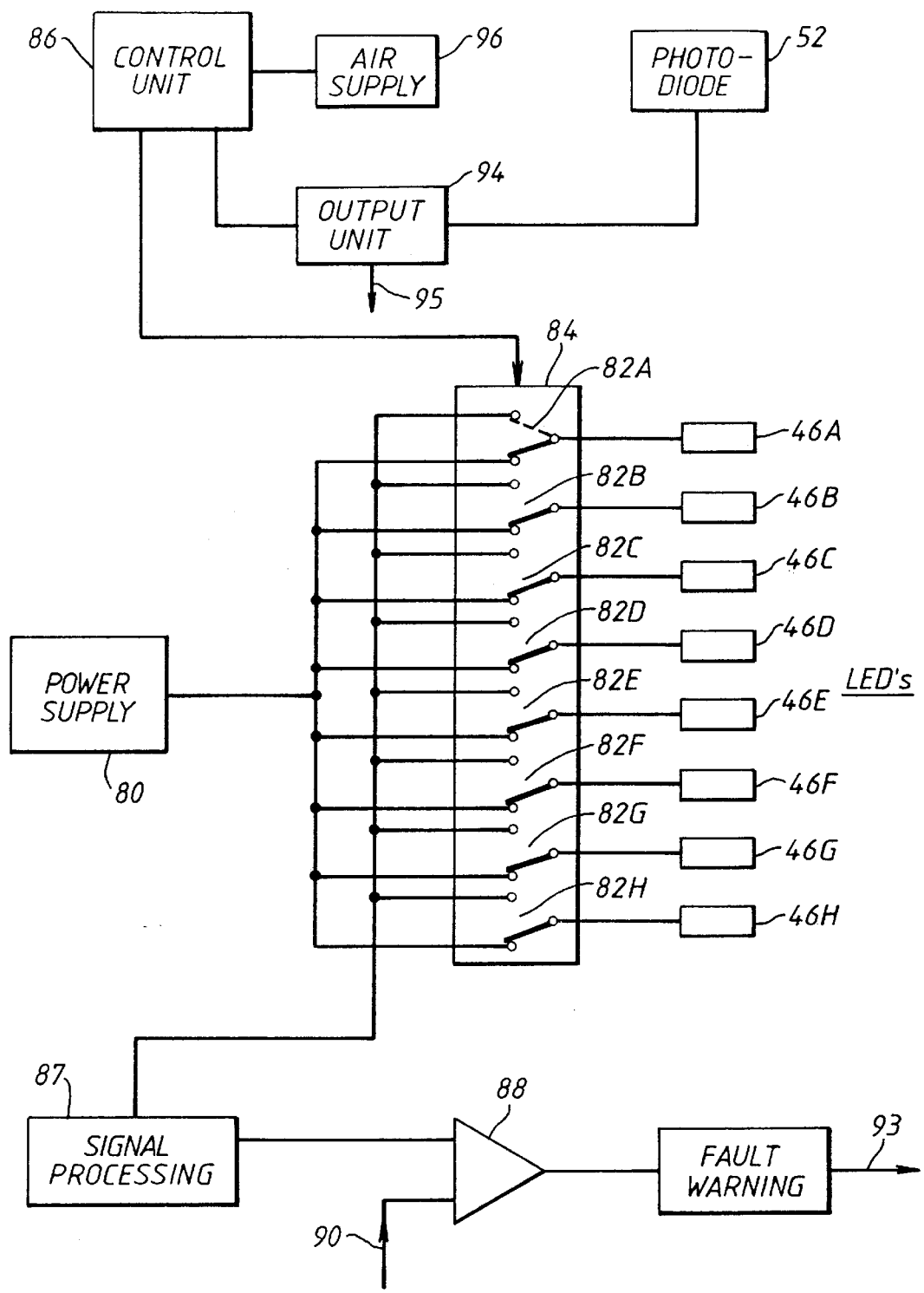
FIG. 4 is a block circuit diagram of part of the apparatus.

FIG. 4 shows, in block diagram form, how the LEDs 46A . . . 46H are energised. Thus, a power supply unit 80 produces a suitable output supply for energising all the LEDs and this is connected to each of the LEDs through respective change-over switches 82A, 82B . . . 82H which are incorporated in a switch unit 84. With the switches 82A to 82H set in the manner shown in FIG. 4, all the LEDs 46A . . . 46H are energised and the apparatus operates to detect oil mist in the manner explained above.

Periodically, however, a control unit 86 switches each of the switches 82A to 82H in turn (one at a time) to the alternate position, as shown dotted for switch 82A. In this position, the LED 46A connected to switch 82A is now connected through a suitable signal processing and amplifying unit 87 to one input of a comparator 88 whose other input receives a reference signal on a line 90. Although LEDs are primarily designed for producing a light output, they will in fact also respond to received light by producing an electrical output voltage. When switch 82A (in this example) is switched to its alternate position, the respective LED 46A will now act as a light sensor for sensing the light received from the diametrically opposed LED 38B, which is of course still energised through the appropriate switch in switch unit 84. The corresponding electrical output produced by LED 46A is thus compared in comparator 88 with the reference level on line 90. If the light output is below a predetermined level, a fault warning unit 92 produces a warning output on a line 93. Such a warning output is thus indicative of the presence of the excessive contamination in the light path between LEDs 46A and 46B (or, of course, a fault in one of these LEDs).

When LED 46A has been tested in this way, the control unit 86 changes switch 82A back to its previous setting and switches switch 82B to the alternate setting. The testing process is repeated, and, of course, subsequently for all the other LEDs.

FIG. 4 shows the photo-diode 52 whose output is connected to an output unit 94 which monitors the output signal from the photo-diode and produces a warning output on a line 95 when particulate contamination is detected in the manner already explained. Such a warning output can be used to shut the engine down and to produce an indication of incipient explosion risk.

Periodically, the control unit 86 energises an air supply unit 96 which provides a supply of clean air through the clean air inlet 74 (FIG. 1). This clean air is directed around the photo-diode 52 (see FIG. 1) and passes through the viewing aperture 56 into the interior of the measuring chamber 60. In passing through the viewing aperture 56, it removes any contamination, such as oil drops, which may become deposited on the sharp edge of the aperture and which might otherwise adversely affect the sensing ability of the photo-diode 52 and/or possibly refract light from the LEDs.

In addition, however, the clean air within the measuring chamber 34 provides a zero level of contamination which is used to normalise the operation of the photo-diode 52. At the same time as energising the air supply 96, the control unit activates the output unit 94 to switch it into a normalising mode. In this mode, it measures the output signal from the photo-diode 52 and adjusts it to a predetermined datum level corresponding to the absence of contamination.

In FIG. 4, the various connections between the individual units and the power supply 80 are omitted for clarity (except for the connection to the LEDs via the switches 82A . . . 82H).

One advantageous form which the cyclone 26 of FIG. 1 can take will now be described with reference to FIG. 2. FIG. 2 illustrates the section 6 of the apparatus of FIG. 1 in slightly modified form, items in FIG. 2 corresponding to those in FIG. 1 being similarly referenced. As shown, the cyclone comprises a cylindrical bore 100 extending radially inwardly of the body of section 6 and intersecting with inlet and outlet bores 102 and 104. Inlet bore 102 is in communication with the inlet 16.

A pin 106, preferably made of metal, is removably mounted within the bore 100 by means of a screw thread 108. It has a narrowed shank 110 around which is thus provided an annular chamber 112 which is in communication with the inlet and outlet bores 102,104.

Incoming air, through inlet bore 102, strikes the shank 110 of the pin 106 in a radial direction. Large drops of oil or other gross contamination will thus be deposited on the shank 110 and will remain there. The air flow, and any smaller particles, will be directed in a generally circular direction around the shank of the pin 106 and will pass repeatedly around the shank and then exit through the outlet bore 104. During this circular motion, centrifugal force will tend to cause other particles of oil to be deposited on the cylindrical wall of the annular chamber 112. Oil mist and small particles will continue unaffected through the outlet bore 104 into the receiving chamber 30 (FIG. 1).

It is a simple matter to remove the pin 106 periodically to clean or replace it.

Figure 2:
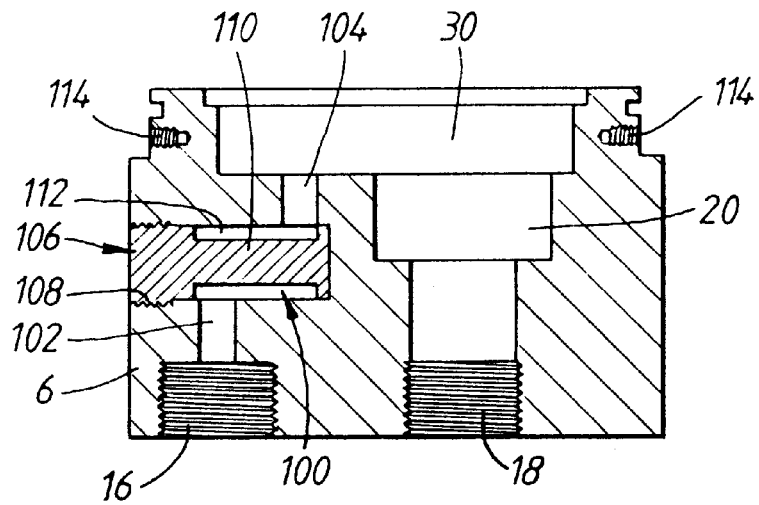
FIG. 2 is a cross-section through part of the apparatus of FIG. 1, showing it in greater detail.

The modified section 6 shown in FIG. 2 is attached to the upper section 5 by bolts which engage in threaded recesses 114.

In certain circumstances, it may be advantageous to arrange the section 6 so that the cyclone is mounted vertically rather than horizontally. This allows oil to drain from it under gravity.

In use, the section 6 (FIG. 1 or 2) can be connected to the engine by means of suitable pipes secured to the inlet 16 and the outlet 18. Instead, it may be directly mounted on the engine.

In a large installation, such as in the engine room of a ship, where the possible presence of oil mist in each of a number of different locations has to be monitored, separate units, each as described with reference to FIG. 1, may be mounted at each of the locations to be monitored, and it is thus only necessary to make simple electrical connections between them and a central monitoring and power supply point.

Because the apparatus is in the form of two easily separable sections, the upper section 5 and the lower section 6, maintenance and repair is simplified. In the event of the detection of excessive contamination in the measuring chamber 34, for example, the corresponding section 5 can simply be removed and replaced by a new or serviced section, the defective one then being taken away for cleaning and servicing or repair.

The LEDs can be replaced by other suitable light emitting devices which are switchable into a mode in which they produce an output in response to received light. The term "light" as used in this specification includes non-visible radiation of a type capable of being scattered by the particles to be detected.

What is claimed is:

1. A particle detecting apparatus for detecting the presence of particles in a gaseous fluid, comprising
 a measuring chamber for receiving the gaseous fluid and defined by wall means,
 light sensing means having a field of view extending in the chamber,
 means for defining a sampling volume in the chamber,
 means for defining a light path in the chamber and which intersects the sampling volume,
 at least one pair of light emitters mounted to direct emitted light across the chamber in opposite directions along the light path towards the sampling volume, whereby particles carried by the gaseous fluid into the sampling volume scatter some of the light therein for detection by the light sensing means,
 the light emitters of the pair normally simultaneously emitting light and at least one thereof having a selectable light detecting mode, and
 control means operative intermittently to switch said one of the light emitters into the light detecting mode so that said one light emitter when switched into the light detecting mode responds to light directly received from the other emitter of the pair along the light path and produces a corresponding output which is dependent on contamination in the light path.

2. The apparatus according to claim 1, including monitoring means for monitoring the output produced by the light emitter when in the light detecting mode, whereby to detect the contamination in the light path.

3. The apparatus according to claim 1, in which the light sensing means is positioned to have a field of view extending axially along the sensing chamber towards the sampling volume.

4. The apparatus according to claim 3, in which the measuring chamber has an open end for receipt of the gaseous fluid and the field of view extends to that open end.

5. The apparatus according to claim 1, including
 means defining a second light path in the chamber,
 at least one further pair of light emitters mounted to direct light across the measuring chamber towards each other in opposite directions along the second light path, and
 control means operative intermittently to switch one of the light emitters of the further pair into a light detecting mode in which it responds to light received from the other emitter of that pair along the second light path to produce a corresponding output which is dependent on contamination in the second light path.

6. The apparatus according to claim 1, including means defining a restricted viewing aperture for the light sensing means.

7. The apparatus according to claim 1, in which the light emitters are mounted in recesses in the wall means.

8. The apparatus according to claim 7, including light-transparent screening means positioned within the chamber adjacent the wall means to protect the light emitters from contamination.

9. The apparatus according to claim 8, in which the screening means is removable.

10. The apparatus according to claim 8, in which the chamber is cylindrical and the screening means is a glass tube.

11. The apparatus according to claim 7, including means for temporarily passing clean air or gas in an axial direction through the chamber and through the viewing aperture.

12. The apparatus according to claim 1, including
means for temporarily passing clean air or gas through the chamber, and
means for monitoring the output of the light sensing means in the presence of this clean air or gas and for setting the output to a predetermined datum level.

13. The apparatus according to claim 1, in which the light emitters are respective light emitting diodes.

14. The apparatus according to claim 1, including
gaseous fluid input/output means having a gaseous fluid inlet for connection to an area being monitored,
a receiving chamber for receiving gaseous fluid drawn in through the inlet, and
an outlet for exhaustion of the gaseous fluid from the receiving chamber,
the receiving chamber being mounted in juxtaposition with the measuring chamber whereby gaseous fluid and particles therein in the receiving chamber tend to diffuse into the measuring chamber.

15. The apparatus according to claim 14, including a diffusion screen between the receiving chamber and the measuring chamber, the diffusion screen being adapted to tend to trap particulate matter not required to be detected.

16. The apparatus according to claim 15, in which the diffusion screen comprises means defining a plurality of tubular passageways, each passageway having a length which is long in relation to passageway width, the lengths of the passageway are generally parallel to each other and extend towards the measuring chamber.

17. The apparatus according to claim 14, in which the gaseous fluid input/output means includes cyclone means positioned between the inlet and the receiving chamber for directing the gaseous fluid along a generally circular path whereby particulates not intended to be detected tend to be deposited by centrifugal action.

18. Apparatus according to claim 12, in which the cyclone means comprises inner and outer cylindrical walls arranged coaxially to define an annular chamber, and
means defining an entrance into the annular chamber and an exit therefrom,
the entrance being connected to the said inlet and the exit being connected to the receiving chamber,
the entrance and exit being spaced axially along the annular chamber,
the entrance extending in a radial direction with respect to the annular chamber whereby gaseous fluid entering the chamber is directed in a generally circular direction around the annular chamber from the entrance to the exit and the said particulates not intended to be detected tend to be deposited at least on the outer wall of the annular chamber by the centrifugal force.

19. The apparatus according to claim 14, in which the gaseous fluid input/output means includes gaseous fluid pumping means.

20. The apparatus according to claim 19, in which the gaseous fluid pumping means is driven electrically, and including detecting means for detecting mal-operation thereof.

21. The apparatus according to claim 14, in which the measuring chamber is mounted in a first housing and the gaseous fluid input/output means is mounted in a second housing, the first and second housings being removably attached to each other.

22. A particle detecting apparatus for detecting the presence of particles in a gaseous fluid, comprising
a measuring chamber for receiving the gaseous fluid and defined by wall means,
light sensing means having a field of view extending in the chamber,
means for defining a sampling volume in the chamber,
means for defining a light path in the chamber and which intersects the sampling volume,
at least one pair of light emitters to direct emitted light across the chamber in opposite directions along the light path towards the sampling volume, whereby particles carried by the gaseous fluid into the sampling volume scatter some of the light therein for detection by the light sensing means,
the light emitter of the pair normally simultaneously emitting light and at least one thereof having a selectable light detecting mode, and
control means operative intermittently to switch one of the light emitters into the light detecting mode so that said one light emitter when switched into the light detecting mode responds to light directly received from the other emitter of the pair along the light path and produces a corresponding output which is dependent on contamination in the light path,
gaseous fluid input/output means having a gaseous fluid inlet for connection to an area being monitored,
a receiving chamber for receiving gaseous fluid drawn in through the inlet, and
an outlet for exhaustion of the gaseous fluid from the receiving chamber,
the receiving chamber being mounted in juxtaposition with the measuring chamber whereby gaseous fluid and particles therein in the receiving chamber tend to diffuse into the measuring chamber.

23. The apparatus according to claim 22, including a diffusion screen between the receiving chamber and measuring chamber, the diffusion screen being adapted to tend to trap particulate matter not required to be detected.

24. The apparatus according to claim 23, in which the diffusion screen comprises means defining a plurality of tubular passageways, each passageway having a length which is large in relation to the passageway width, the lengths of the passageways being generally parallel and extending towards the measuring chamber.

25. The apparatus according to claim 22, in which the gaseous fluid input/output means includes cyclone means positioned between the inlet and the receiving chamber for directing the gaseous fluid along a generally circular path whereby particulates not intended to be detected tend to be deposited by centrifugal action.

26. Apparatus according to claim 25, in which the cyclone means comprises inner and outer cylindrical walls arranged coaxially to define an annular chamber, and
means defining an entrance into the annular chamber and an exit therefrom,
the entrance being connected to the said inlet and the exit being connected to the receiving chamber, the entrance and exit being spaced axially along the annular chamber, the entrance extending in a radial direction with respect to the annular chamber whereby gaseous fluid entering the chamber is directed in a generally circular direction around the annular chamber from the entrance to the exit and the said particulates not intended to be detected tend to be deposited at least on the outer wall of the annular chamber by the centrifugal force.

27. The apparatus according to claim 22, in which the gaseous fluid input/output means includes gaseous fluid pumping means.

28. The apparatus according to claim 27, in which the gaseous fluid pumping means is driven electrically, and including detecting means for detecting mal-operation thereof.

29. The apparatus according to claim 22, in which the measuring chamber is mounted in a first housing and the gaseous fluid input/output means is mounted in a second housing, the first and second housing being removably attached to each other.

* * * * *